United States Patent [19]
Knute

[11] 3,994,294
[45] Nov. 30, 1976

[54] SYRINGE PUMP VALVING AND MOTOR DIRECTION CONTROL SYSTEM

[75] Inventor: Wallace L. Knute, Solana Beach, Calif.

[73] Assignee: Ivac Corporation, San Diego, Calif.

[22] Filed: Feb. 28, 1975

[21] Appl. No.: 554,091

[52] U.S. Cl. .......................... 128/214 F; 128/234; 128/274; 128/DIG. 12; 222/450; 251/9; 417/19; 417/317; 417/510
[51] Int. Cl.[2] .......................................... A61M 5/20
[58] Field of Search......... 128/214 R, 214 B, 214 E, 128/214 F, 214.2, 218 A, 234, 273, 274, DIG. 12, DIG. 13; 251/7, 9; 417/317, 510, 18, 19; 222/309, 450

[56] References Cited
UNITED STATES PATENTS

| | | | |
|---|---|---|---|
| 2,625,932 | 1/1953 | Salisbury | 128/214.2 |
| 2,625,933 | 1/1953 | Salisbury | 128/214.2 |
| 3,359,910 | 12/1967 | Latham | 417/478 X |
| 3,543,752 | 12/1970 | Hesse et al. | 128/214 E |
| 3,550,619 | 12/1970 | Halasz et al. | 251/7 |
| 3,654,959 | 4/1972 | Kassel | 251/9 X |
| 3,731,679 | 5/1973 | Wilhelmson et al. | 128/214 F |
| 3,963,151 | 6/1976 | North | 251/9 X |

FOREIGN PATENTS OR APPLICATIONS

| | | | |
|---|---|---|---|
| 637,504 | 1/1928 | France | 128/214 R |

*Primary Examiner*—Dalton L. Truluck
*Attorney, Agent, or Firm*—Fulwider, Patton, Rieber, Lee & Utecht

[57] ABSTRACT

Apparatus for fluid flow control in a parenteral administration system, utilizing a syringe pump operated by a motor to repetitively fill and empty a syringe cartridge over a plurality of operational cycles of successive fill stroke and pump stroke periods. The apparatus repetitively and sequentially opens and closes a pair of intake and output I.V. tubes communicating with a syringe, the tubes alternating opened and closed states, one tube always being open while the other is closed, by means of a pair of L-shaped pivotal tube pinchers, one pincher controlling each I.V. tube, each pincher being normally spring biased to the tube clamping shut-off state. The tube pinchers are alternately pivoted to a non-clamping, tube-open position by a spring biased, intermittent motion, reciprocating slide bar under the control of a reversible, rotating cam, the cam being driven by the same motor as that used to drive the piston of the syringe through its fill and pump strokes. A photoelectric sensor is responsive to the physical position of one of the tube pinchers and generates an electrical signal to control the direction of motor rotation and, hence, determines whether the syringe pump performs a fill stroke or a pump stroke.

34 Claims, 6 Drawing Figures

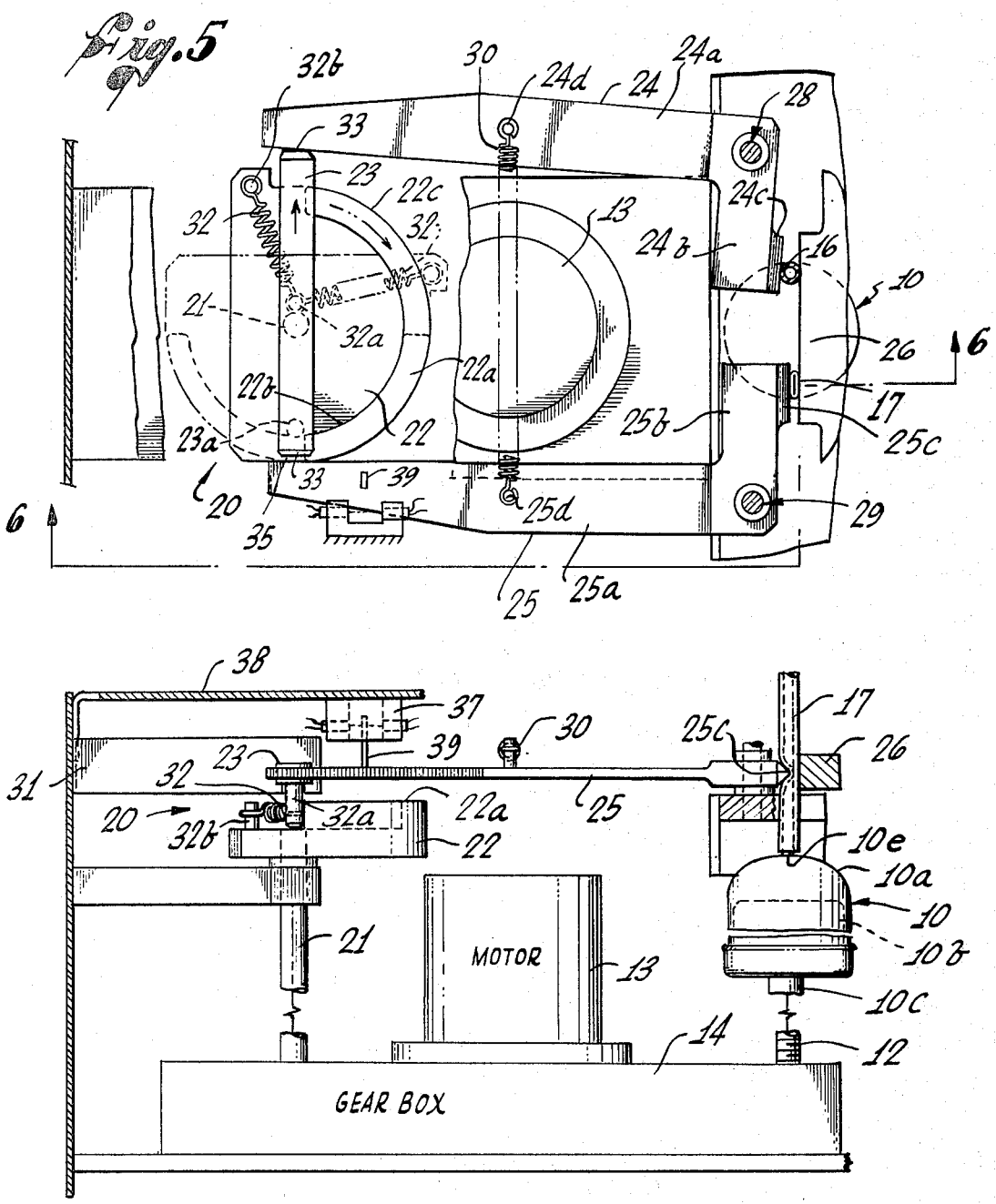

SYRINGE PUMP VALVING AND MOTOR DIRECTION CONTROL SYSTEM

BACKGROUND OF THE INVENTION

This invention relates generally to improvements in syringe pumps and, more particularly, to a new and improved valve control system for such pumps which reliably and precisely opens and closes the intake and output I.V. tubes for a syringe at appropriate points in the pumping cycle and also generates a control signal for establishing direction of motor rotation.

The usual medical procedure for the gradual parenteral admisistration of liquids into the human body, such as liquid nutrients, blood or plasma, makes use of apparatus which is commonly referred to in the medical arts as an intravenous administration set. The intravenous set usually comprises a botttle of liquid, normally supported in an inverted position, an intravenous feeding tube, trypically of clear plastic, and a suitable valve mechanism, such as a roll clamp, which allows the liquid to drip out of the bottle at a selectively adjustable rate into a transparent drip chamber below the bottle. The drip chamber serves the dual function of allowing a nurse or other attendant to observe the rate at which the liquid drips out of the bottle, and also creates a reservoir for the liquid at the lower end of the drip chamber to insure that no air enters the main feeding tube leading to the patient.

While observation of the rate of drop flow via the drip chamber is a simple way of controlling the amount of liquid fed to a patient over a period of time, its ultimate effectiveness requires that a relatively constant vigil be maintained on the drop flow, lest it cease entirely due to exhaustion of the liquid supplied or become a continuous stream and perhaps increase the rate of liquid introduction to the patient to dangerous levels.

By way of example, it has been the general practice in hospitals to have nurses periodically monitor drop flow rate at each intravenous feeding or parenteral infusion station. Such monitoring of drop flow is a tedious, and time consuming process, prone to error and associated, possibly serious consequences, and resulting in a substantial reduction of the available time of qualified medical personnel for other important duties. Typically, the nurse monitoring drop flow rate will use a watch to time the number of drops flowing in an interval of one or more minutes, and she will then mentally perform the mathematics necessary to convert the observed data to an appropriate fluid flow rate, e.g., in drops per minute. If the calculated flow rate is substantially different than the prescribed rate, the nurse must manually adjust the roll clamp for a new rate, count drops again, and recalculate to measure the new flow rate.

Obviously, each of the aforedescribed measurements, calculations and flow rate adjustments usually take several minutes time which, when multiplied by the number of stations being monitored and the number of times each station should be monitored per day, can result in a substantial percentage of total personnel time available. In addition, under the pressure of a heavy schedule, the observations and calculations performed by a harried nurse in measuring and adjusting flow rate may not always prove to be reliable and, hence, errors do occur resulting in undesired, possibly dangerous infusion flow rates.

In addition to the aforedescribed difficulties, the parenteral administration of medical liquids by gravity induced hydrostatic pressure infusion of the liquid from a bottle or other container suspended above the patient, is very susceptible to fluid flow rate variation due to changes in the liquid level in the bottle, changes in temperature, changes in the venous or arterial pressure of the patient, patient movement, and drift in the effective setting of the roll clamp or other valve mechanism pinching the feeding tube. Moreover, there are a number of situations, such as in intensive care, cardiac and pediatric patients, or where rather potent drugs are being administered, where the desired drop flow rate must be capable of very precise selection.

It will be apparent, therefore, that some of the most critical problems confronting hospital personnel faced with an overwhelming duty schedule and limited time availability are the problems of quickly, easily, reliably and accurately monitoring and regulating flow rates in the parenteral administration of medical liquids.

In recent years, a number of electrical monitoring systems, drop flow controllers and infusion pumps have been developed to accomplish the various tasks of sensing and regulating drop flow rates. However, while such monitoring and drop rate control devices have generally served their purpose, they have not always proven entirely satisfactory from the standpoint of cost, complexity, stability, reliability, accuracy, or precision of adjustment over a wide range of selected flow rates. In addition, such systems have sometimes been subject to drift and substantial flow rate variations due to changes in temperature, feeding tube crimps, variations in venous or arterial pressure of the patient, or variations in the height of the bottle or solution level within the bottle. Substantial difficulties have also been experienced particularly in connection with establishing and maintaining accurate flow at very low flow rates.

Positive pressure pumps of the closed-loop peristaltic type have been provided which overcome some of the aforementioned difficulties with regard to drift, and accurate flow at low flow rates. However, even such closed-loop positive pressure systems only serve to maintain accuracy of flow in terms of stabilizing to a preselected drop flow rate, rather than delivering a precise preselected volume of fluid, e.g., in cubic centimeters per hour. The reason for this is that the accuracy of such a system is limited inherently to the accuracy of the size of the drops produced by an intravenous administration set, and the actual drops produced by the latter apparatus can vary rather substantially from its designated drop size, e.g., due to drip chamber structural variations, by as much as thirty percent.

More recently, positive pressure infusion pumps of the syringe type have also been provided, wherein a syringe having a very precise displacement volume is repeatedly filled and emptied on alternate syringe piston strokes during a combined "fill" and "pump" operational cycle, so that control of the rate at which the syringe is filled and emptied provides an accurate means for precise fluid volume delivery over a prescribed period of time. Such syringe pumps are essentially independent of drop flow inaccuracies introduced by I.V. administration sets and appear to provide the best overall solution to accurate and stable fluid volume delivery over long periods of time, at both high and low flow rates. However, since a portion of each operating cycle with such syringe pumps is concerned with filling the syringe, rather than delivering fluid to the patient in a pumping mode, there is a need for extremely precise control over the intake and output syringe valving and the direction of rotation of the motor driving the syringe. Such valve control must not only be very positive in its action and extremely accurate in its timing, but must also be in precise synchronism with the control over motor direction.

In addition, syringe pumps of the prior art primarily depend on valving embodied directly within the syringe itself. This not only increases the cost and complexity of the syringe, particularly where disposable syringes are employed, but usually also results in reduced reliability of operation.

Hence, those concerned with the development and use of parenteral fluid administration systems, and particularly those concerned with the design of syringe pumps, have long recognized the need for improved, relatively simple, economical, reliable, stable and accurate valving and motor control systems for such syringe pumps. The present invention clearly fulfills this need.

SUMMARY OF THE INVENTION

Briefly, and in general terms, the present invention provides a new and improved system for accurately controlling fluid flow in the parenteral administration of medical liquids, wherein the repetitive opening and closing of a pair of intake and output I.V. tubes communicating with a syringe is automatically accomplished during successive fill and pump periods by means of cam control of a pair of pivotal tube pinchers which alternately pinch off and open the intake and output tubes in proper sequence. In addition, the physical position of one of the tube pinchers is monitored and controls the direction of rotation of the pump motor and, hence, determines the fill or pump mode of operation of the syringe. Such valving and motor direction control is accomplished with no lost motion or delay, in that the valving action and motor direction changes are automatically maintained in precise synchronism. Moreover, valving is provided without the need for providing relatively complex, expensive and sometimes unreliable valve structures in the syringe itself.

More particularly, the present invention provides a new and improved syringe pump embodying a reversible, rotary cam controlled reciprocating slide bar for alternately moving each of a pair of tube pinchers to successively clamp off and open the intake and output I.V. tubes of the syringe to fluid flow, and, further, controlling motor direction in synchronism with the sequential open and closed states of the I.V. tubes, to properly enable performance of successive cycles of fill and pump strokes.

The rotary cam includes an arcuate ridge adjacent its outer periphery defining semi-circular inner and outer camming surfaces against which a cam follower is biased, the cam follower being held against one camming surface during performance of a pump stroke and against the other camming surface during performance of a fill stroke, the cam follower typically being in the form of a pin secured to and projecting from one side of a slide bar which reciprocates intermittently back and forth in a guide block, along a linear path. Each movement of the slide bar coincides with a change from a fill stroke to a pump stroke, or from a pump stroke to a fill stroke, in the overall operational cycle of the syringe pump.

Both tube pinchers are pivotally mounted and spring biased towards each other and towards the tube clamping state. The slide bar is power driven by an extension spring. During performance of each syringe stroke, the cam surface engaging the slide bar pin holds the slide bar against the appropriate tube pincher to pivot the latter and hold it in the tube-open position, thereby relieving the slide bar spring of the task of overcoming the pincher spring during performance of each syringe stroke. In addition, during the transition period between syringe strokes, the slide bar spring is initially assisted in its movement by the pincher spring, the slide bar spring only having to work against the pincher spring in the latter portion of the slide bar stroke when the slide bar has already acquired some momentum.

The slide bar center is offset from the center of rotation of the cam, at the end of each slide bar stroke repositioning the pinchers. In this regard, one end of the slide bar spring is secured to the center of the slide bar, while the other end is secured to a point along the outer periphery of the rotary cam. Therefore, as the cam rotates, with the slide bar held stationary (since the slide bar pin is biased against either the inner or outer arcuate camming surface), the slide bar spring is tensioned and suddenly released, to shift the slide bar longitudinally and reposition the tube pinchers, only when the slide bar pin cam follower comes to the end of the arcuate camming surface and drops off to move either from the inner camming surface to the outer camming surface, or from the outer surface to the inner surface of the cam, depending upon the particular syringe stroke just completed. Then the cam begins to turn in the opposite direction, again trapping the slide bar cam follower pin to maintain the slide bar in a fixed position while stretching and rotating the slide bar extension spring. When the latter spring has been fully stretched and rotated 180° to cock the slide bar mechanism, the other end of the arcuate ridge on the cam goes past the slide bar pin, allowing the slide bar to snap over to its alternate position and begin the entire cycle over again.

A fixed light source and photoelectric sensor arrangement provides a reference light beam which is selectively interrupted by an opaque flag carried on one of the tube pinchers. The flag is repositioned each time the tube pincher on which it is mounted is moved, so that a control signal is developed indicative of the syringe stroke about to be performed, the control signal being used to establish the proper direction of rotation of the motor.

The new and improved syringe pump valving and motor direction control system of the present invention is extremely accurate and reliable. The system provides valve control without the need for separate valves in the syringe itself and provides precise motor direction control in perfect synchronism with the opening and closing of the syringe intake and output lines.

The above and other objects and advantages of the present invention will become apparent from the following more detailed description, when taken in conjunction with the accompanying drawings of an illustrative embodiment.

DESCRIPTION OF THE DRAWINGS

FIG. 5 is a plan view similar to FIG. 2, and illustrates the state of the apparatus during performance of a fill stroke; and FIG. 6 is a combined elevational and sectional view, taken along the line 6—6 in FIG. 5.

DESCRIPTION OF THE PREFERRED EMBODIMENT

Figure 1:
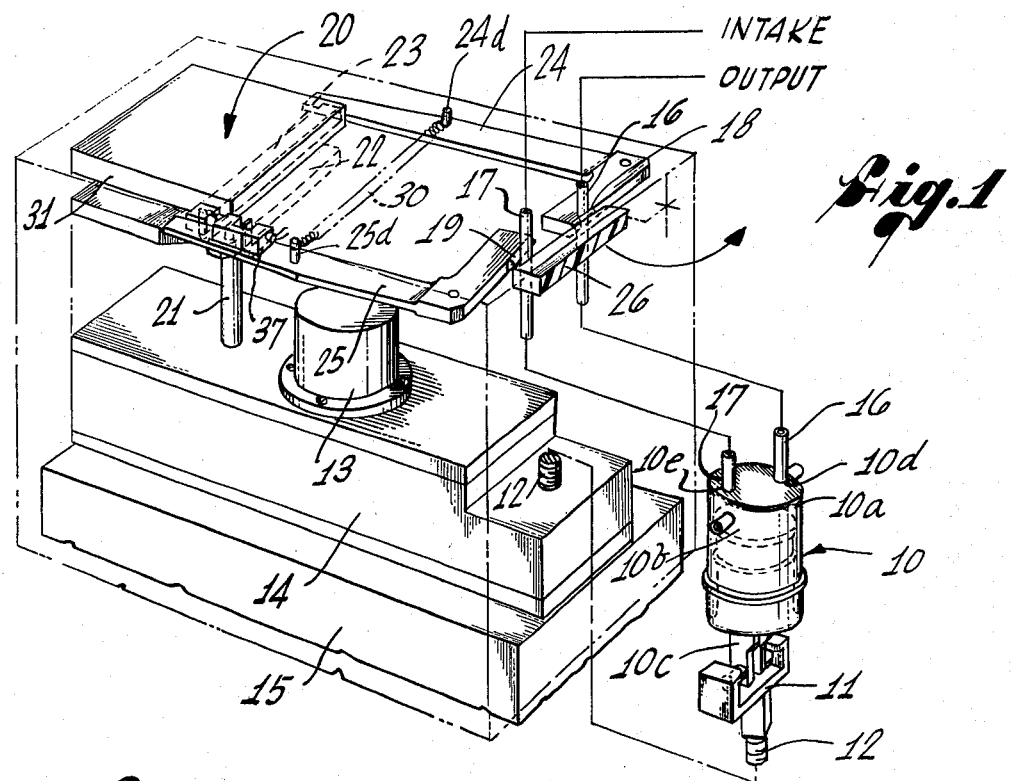
FIG. 1 is a perspective view showing the interior structure of a syringe pump embodying the present invention, the outer pump housing being shown in dashed lines.

Referring now to the drawings, there is shown a syringe pump system for fluid flow control, embodying the features of the present invention. In the ensuing description, while reference is made to the term "I.V.", normally connoting intravenous administration, it is to be understood that this is by way of example only, and the system of the present invention is suitable for other forms of parenteral administration as well as intravenous administration.

The system shown in FIG. 1 depicts a syringe pump embodying a syringe 10 which preferably is in the form of a disposable cartridge, but it will become apparent that all of the features of the present invention may be practiced independently of whether or not the syringe 10 is disposable. The syringe 10 essentially includes a molded cylinder 10a in which a piston 10b is slidably received and adapted to be reciprocated back and forth along the axis of the cylinder by an integral piston rod 10c which is removably mounted at one end in a coupling shoe 11 carried by a lead screw 12 which is advanced and retracted by a suitable drive system. The drive system includes a reversible, d.c. stepping motor 13 and appropriate gearing 14, to drive the lead screw 12 which is, in turn, coupled to the piston rod 10c of the syringe 10. The motor 13 is energized by a pulse train of motor drive pulses generated by an appropriate electrical control system 15.

The syringe 10 includes an inlet port 10d and an outlet port 10e. The inlet port 10d communicates through a suitable intake I.V. tube 16 with any appropriate liquid source (not shown), usually an I.V. bottle containing appropriate drugs and/or nutrients in fluid form. Typically, the intake I.V. tube 16 is part of an I.V. administration set which includes a transparent drip chamber in the line between the syringe 10 and the liquid source.

A similar, output I.V. tube 17 is connected at one end to the outlet port 10e of the syringe 10 and conveys fluid from the syringe to a patient.

A pair of syringe pump valves 18, 19, external to the syringe 10, are of the tube pincher type, and are selectively opened and closed at appropriate times in the overall pumping cycle, under the control of a suitable valve control system 20. The valve 18 controls the inlet port 10d and is open during the fill stroke to enable fluid to be drawn from the liquid source, through the intake line 16, into the syringe 10, the valve 18 being closed during the pump stroke to prevent fluid from exiting the syringe through the inlet port. The valve 19 controls the outlet port 10e and is open during the pump stroke to enable fluid delivery from the syringe 10 to the patient through the output line 17, the valve 19 being closed during the fill stroke.

The valve control system 20 is also driven, through the gearing 14, by the same drive motor 13 as is used to operate the syringe 10. The valve control system 20 also provides information to the electrical control system 15 controlling the motor 13, indicating that the syringe 10 is either in the fill stroke or the pump stroke, and this information, in turn, enables the electrical control system to establish the proper direction of rotation of the motor. The electrical control system 15 may be of conventional design for electrically energizing the motor 13 and controlling its direction of rotation, or the control system may be of the form described in copending application, Ser. No. 554,092, entitled Fluid Flow Control System, inventor Heinz W. Georgi, filed Feb. 28, 1965, and assigned to the same assignee as the present application. A copy of the specification and drawings for the latter application is attached hereto as Appendix A.

The motor 13 drives, through the gearing 14 and an output camshaft 21, a reversible, semi-circular rotary cam 22 which controls the opened and closed positions of the syringe pump valves 18, 19.

The gear ratio of the gearing 14 is specifically selected so that the rotary cam 22 rotates through an angle of approximately 180° during a pump stroke of the syringe 10, and then reverses and rotates through another 180° in the opposite direction during an intake stroke. Hence, the rotary cam 22 is essentially a half-turn cam. The camshaft 21 rotates the cam 22 which biases a slide bar 23 to alternately hold one syringe pump valve open and then the other, in proper cyclical sequence.

The syringe pump valves 18, 19 consist of a pair of pivotal tube pinchers 24, 25 which alternatively pinch off and open the intake and output tubes 16, 17 respectively, of the syringe 10. The tube pinchers 24, 25 are spring biased to the tube shut-off position and are positively driven open by the valve control system 20, thus allowing full tube closure regardless of normal variations in I.V. tubing diameter and wall thickness.

As best observed in FIGS. 2–5, each of the tube pinchers 24, 25, is of substantially L-shape and includes a long arm 24a, 25a, respectively, and a short arm 24b, 25b, respectively. One face of the short arm 24b is shaped to define a pincher blade 24c adapted to cooperate with the confronting face of a shoulder 26 defined on the interior side of a syringe pump access door 27 to the syringe compartment. Similarly, a pincher blade 25c is defined by the short arm 25b of the output tube pincher 25. Together, the pincher blades 24c, 25c and the access door shoulder 26 define a pair of clamping surfaces between which the intake and output I.V. tubes 16, 17 pass. The access door 27 is held shut, after the syringe has been installed, by any suitable latch 27a.

The intake tube pincher 24, is pivotally mounted by means of a pivot pin and bushing at 28. Similarly, the output pincher is pivotally mounted at 29. Both tube pinchers are spring-biased to the tube clamping shut-off state by a coil spring 30 extending between the pinchers and appropriately secured at each end to one of the pinchers, as by anchor pins 24d, 25d, respectively.

The syringe pump valves 18, 19 are selectively opened in proper cyclical sequence by pivoting the tube pinchers 24, 25, one at a time, via contact with the reciprocating, intermittent motion slide bar 23 which is power driven by a slide bar extension spring 32. The slide bar 23 is slidably mounted within a guide block 31 and contacts the tube pinchers 24, 25 by bumper pads 33 mounted at each end of the slide bar. In order for the slide bar spring 32 to drive the slide bar 23 in both directions, one end of the slide bar spring is secured to the slide bar at its center, by an anchor pin 32a, while the other end of the slide bar spring is secured to the rotary cam 22 near its outer periphery by an anchor pin 32b. In either of its two positions at the end of a slide bar stroke, the center of the slide bar 23 along its longitudinal axis is offset from the center of rotation of the cam 22.

The slide bar 23 moves only upon completion of a syringe stroke, either a fill stroke or a pump stroke. The slide bar 23 is maintained in a fixed position during performance of any syringe stroke by an arcuate, semicircular ridge 22a on the cam 22 defining inner and outer camming surfaces 22b, 22c respectively, adjacent the outer periphery of the cam, each of these camming surfaces alternately abutting a slide bar pin 23a secured to and projecting from one face of the slide bar at the end of the slide bar.

The slide bar pin 23a is a cam follower which is held against one of the camming surfaces 22b, 22c during performance of each syringe stroke and switches positions from one of these camming surfaces to the other camming surface at the end of each stroke. As the cam 22 rotates, the slide bar spring 32 is tensioned to cock the slide bar mechanism. Since the center of the slide bar 23 does not coincide with the center of the cam 22 in either of the two positions of the slide bar, rotation of the cam causes the slide bar spring 32 to stretch becuase the slide bar center is always repositioned to the opposite side of the cam center when the cam rotates through a 180° cycle. Hence, the slide bar spring 32 is tensioned by turning the cam 22 and yet the cam holds the slide bar 23 in the same position throughout the 180° rotary cycle.

Figure 2:
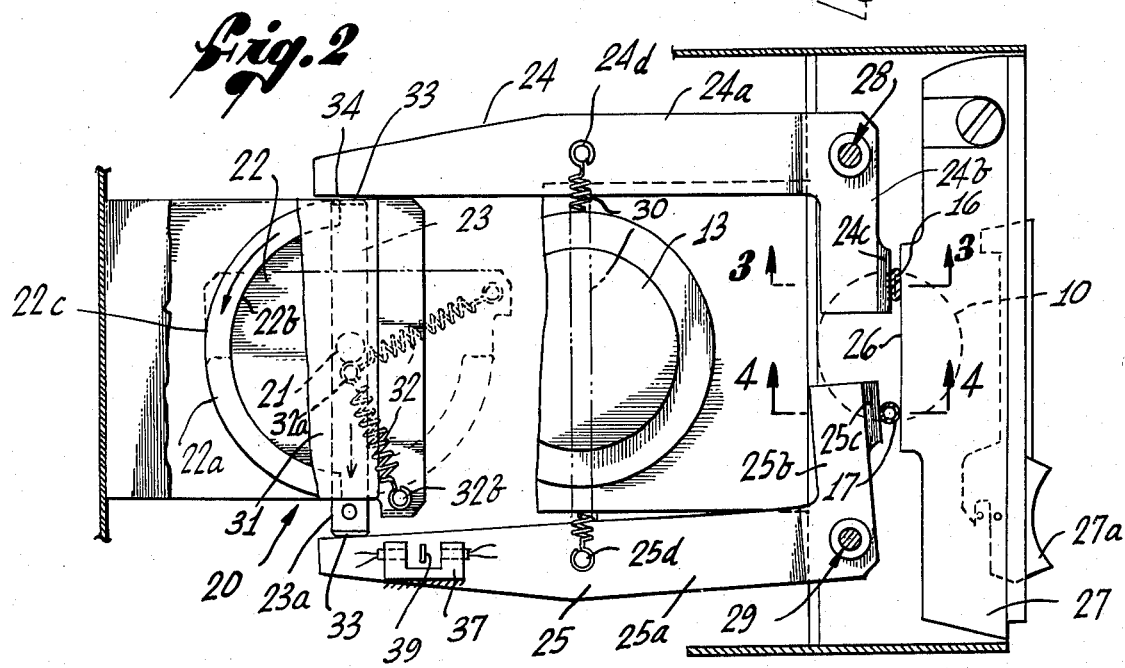
FIG. 2 is an enlarged, plan view, of the syringe pump of FIG. 1 with the top plate removed, and illustrates the apparatus during a pump stroke, sequential positions of the apparatus being shown in phantom.
Figure 3:
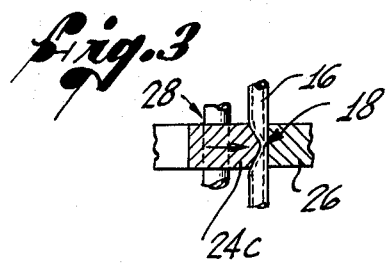
FIG. 3 is a fragmentary sectional view, taken along the line 3—3 in FIG. 2.
Figure 4:
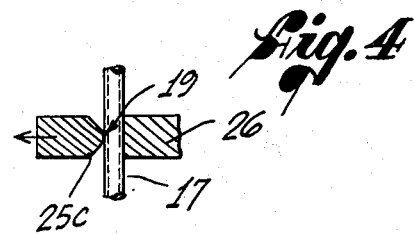
FIG. 4 is a fragmentary sectional view, taken along the line 4—4 in FIG. 2.

As best observed in FIGS. 2 and 5, wherein mid-cycle positions of the rotary cam 22 are shown in phantom, when the end of the ridge 22a on the cam 22 is rotated past the slide bar pin 23a, the slide bar spring 32 snaps the slide bar 23 over from one of its two positions to the other position in performance of a slide bar stroke, causing the tube pinchers 24, 25 to change position. The tube pincher that was previously open, now closes, while the tube pincher that was previously closed now opens. Then the cam 22 begins to turn in the reverse direction, again trapping the slide bar pin 23a against one of the camming surfaces 22b, 22c, to maintain the slide bar 23 in a fixed position while tensioning and rotating the slide bar spring 32. When the slide bar spring 32 has been fully tensioned and rotated 180°, again cocking the slide bar mechanism, the other end of the semi-circular ridge 22a on the cam 22 goes past the slide bar pin 23a, allowing the slide bar 23 to briskly snap over to its alternate position and begin the entire syringe pump cycle again. The result is extremely precise, positive action valving.

In the embodiment of the invention illustrated, the slide bar pin 23a rides on the outer surface 22c of the cam 22 during the pump stroke (FIG. 2) and rides on the inner surface 22b of the cam during the fill stroke (FIG. 5). As the slide bar 23 moves from one position to the other, it pushes one or the other of the tube pinchers 24, 25 open. The tupe pincher spring 30 is what actually provides the tube closure force, i.e., the force necessary to close on the I.V. tubes 16, 17. The slide bar extension spring 32 merely provides a force to drive the slide bar 23 through a slide bar stroke.

One advantage of the valve control system 20 resides in the manner in which the tube pincher spring 30 always holds one of the tube pinchers 24, 25 against the I.V. tubing. As a result, the slide bar spring 32 can move the slide bar 23 and both tube pinchers 24, 25 without having to overcome the tube pincher spring 30 during the entire slide bar stroke. The tube pincher spring 30 is stretched between the pair of tube pinchers 24, 25 and, if the I.V. tubing were not present, it would cause both tube pinchers to rest against both of the bumper pads 31 of the slide bar 23. However, when the I.V. tubing is in place, it causes the closed tube pincher to be spaced a small distance away from the end of the slide bar 23, as at 34 in FIG. 2 and at 35 in FIG. 5. Because of this gap, when the slide bar 23 first starts to move at the end of a syringe fill or pump stroke, the tube pincher spring 30 actually aids the slide bar spring 32 in initially driving the slide bar. Only near the end of the slide bar stroke, when the slide bar 23 has already built up considerable momentum, does the tube pincher spring 30 exert any force tending to retard the motion of the slide bar.

The position of the tube pinchers 24, 25 is sensed by a combined light source and photoelectric sensor assembly 37, which controls the direction of rotation of the motor 13. In this regard, the pincher position sensor assembly 37 is mounted on the underside of the cover plate 38 (FIG. 6) of the pump housing and is thereby supported in a fixed position. An opaque flag 39 is carried by the output tube pincher 25.

As shown in FIG. 2, when the flag 39 interrupts the reference light beam between the light source and photoelectric sensor, an electrical signal is generated indicating that the system is either about to initiate or is already performing a pump stroke, i.e., the output tube 17 is open. In contrast, as observed in FIG. 5, when the flag 39 is retracted by the tube pincher 25, an electrical signal is generated indicating that the system is either about to initiate or is in the performance of a fill stroke, i.e., the intake tubing 16 is open. The motor direction control afforded by such an arrangement is in precise synchronism with the intake and output tube valving and the pump can never cause fluid to be taken in through the syringe output tube 17, or be pumped through the syringe intake tube 16. Moreover, the motor 13 never reverses until the tube pinchers 24, 25 have been actuated. This results in a very precise volume displacement for each syringe stroke.

In summary, when the slide bar pin 23a arrives at the end of the inner camming surface 22b at the completion of a fill stroke, the slide bar pin will drop off the cam 22 because of the force exerted by the tensioned slide bar spring 32, and the pin will then move to the outer camming surface 22c for performance of a pump stroke (FIG. 2). This will reposition the tube pinchers 24, 25 to close the intake tube 16, open the output tube 17, and generate a control signal via the position sensor 37 to reverse the motor 13. Then the cam 22 will reverse, because the motor 13 is reversed, and the cam will rotate while capturing the slide bar pin 23a on its outer camming surface 23c. The cam 22 will go through another 180° cycle in the reverse direction while again stretching the slide bar spring 32, this time because the slide bar center is on the other side of the cam center. At the end of the 180° cycle, the slide bar pin 23a will again drop off the outer camming surface 22c, and move to the inner camming surface 22b where it started (FIG. 5). In this way, the slide bar 23 oscillates intermittently between its two extreme positions to pivot the tube pinchers 24, 25 and open and close the intake and output I.V. tubes 16, 17, precisely and positively at appropriate times in the operational cycle of the syringe pump.

The syringe pump valving and motor direction control system of the present invention satisfies a long existing need for improved, relatively simple, economical, reliable, stable and accurate valving and motor control systems for such syringe pumps. The system provides extremely precise valve control without the need for separate valves in the syringe itself and provides precise motor direction control in perfect synchronism with the opening and closing of the syringe intake and output tubes.

It will be apparent from the foregoing that, while particular forms of the invention have been illustrated and described, various modifications can be made without departing from the spirit and scope of the invention. Accordingly, it is not intended that the invention be limited, except as by the appended claims.

I claim:

1. In a syringe pump having a housing and intake and output I.V. tubes, the combination comprising:
   a pair of movable tube pinchers positioned adjacent the I.V. tubes to normally pinch off the tubes;
   drive means for alternately positioning said tube pinchers to open and close said I.V. tubes in proper sequence for performance of fill and pump strokes by the syringe pump;
   cam means within the housing in the vicinity of said tube pinchers; and
   cam follower means consisting of a single member positioned by said cam means for controlling substantially simultaneouus snap action positioning of both of said tube pinchers so that said positioning maintains a one tube always open and one tube always closed relationship.

2. A combination as set forth in claim 1, and further comprising:
   sensing means responsive to the position of at least one of said tube pinchers for generating an electrical signal to determine whether the next stroke performed by the syringe pump will be a fill stroke or a pump stroke.

3. A combination as set forth in claim 1, and further including:
   a tube pincher spring connected between said tube pinchers and biasing both of said tube pinchers toward the tube closing position.

4. A combination as set forth in claim 1, wherein said cam means includes a pair of camming surfaces, one of said camming surfaces conditioning the syringe pump for performance of a fill stroke, the other of said camming surfaces conditioning the syringe pump for performance of a pump stroke.

5. In a syringe pump having a housing and intake and output I.V. tubes, the combination comprising:
   a pair of movable tube pinchers positioned adjacent the I.V. tubes;
   drive means within the housing for alternately positioning said tube pinchers to open and close the I.V. tubes in proper sequence for performance of fill and pump strokes by the syringe pump, said drive means including a cam and a reciprocating, intermittent motion slide bar located between said tube pinchers and adapted to alternately move said tube pinchers, said slide bar being controlled by said cam.

6. A combination as set forth in claim 5, wherein said slide bar reciprocates between two positions, and each end of said slide bar alternately contacts or is spaced away from the adjacent one of said tube pinchers depending upon which of said two positions is assumed by said slide bar.

7. A combination as set forth in claim 6, and further including:
   means for rotating said cam;
   a tube pincher spring connected between said tube pinchers and biasing both of said tube pinchers toward the tube closing position; and
   a slide bar spring, controlled by said cam, for driving said slide bar between said two positions.

8. A combination as set forth in claim 1, wherein said cam includes a pair of camming surfaces for tensioning said slide bar spring while maintaining said slide bar in one or the other of said two positions, one of said camming surfaces conditioning the syringe pump for performance of a fill stroke, the other of said camming surfaces conditioning the syringe pump for performance of a pump stroke.

9. A combination as set forth in claim 8, wherein the center of said slide bar is offset from the center of rotation of said cam in either of said two positions of said slide bar.

10. A combination as set forth in claim 9, and further including:
    tube pincher position sensing means for controlling the direction of rotation of said cam.

11. In a system for parental administration of liquids from a liquid source to a patient, apparatus comprising:
    a housing;
    syringe means supported by said housing for performing alternate fill and pump strokes to control the flow of liquid to a patient, said syringe means including intake and output I.V. tubes;
    a pair of movable tube pinchers adjacent said I.V. tubes, one for each of said I.V. tubes, for alternately clamping off and opening the associated I.V. tube;
    motor means within said housing for driving said syringe means for performance of said fill and pump strokes;
    valve control means within said housing for alternately positioning said tube pinchers to periodically open and close said I.V. tubes at appropriate times to enable said syringe means to sequentially perform said fill and pump strokes, said valve control means including a slide bar adapted to move along a linear path between said tube pinchers to alternately move one of said tube pinchers and then the other of said tube pinchers to the tube open position, said slide bar reciprocating between two positions, each end of said slide bar alternately contacting or being spaced away from the adjacent one of said tube pinchers depending upon which of said two positions is assumed by said slide bar;
    a rotary cam adapted to be rotated by said motor means;
    a tube pincher spring connected between said tube pinchers and biasing both of said tube pinchers toward the tube closing position; and a slide bar spring, controlled by said cam, for driving said slide bar between said two positions.

12. Apparatus as set forth in claim 11, wherein said cam includes a pair of camming surfaces for tensioning said slide bar spring while maintaining said slide bar in one or the other of said two positions, one of said camming surfaces conditioning the syringe pump for performance fo a fill stroke, the other of said camming surfaces conditioning the syringe pump for performance of a pump stroke.

13. In a system for parenteral administration of liquids from a liquid source to a patient, apparatus comprising:
a housing;
syringe means supported by said housing for performing alternate fill and pump strokes to control the flow of liquid to a patient, said syringe means including intake and output I.V. tubes;
a pair of spring biased movable tube pinchers adjacent said I.V. tubes, one for each of said I.V. tubes, for alternately clamping off and opening the associated I.V. tube;
motor means within said housing for driving said syringe means for performance of said fill and pump strokes; and
valve control means within said housing for alternately positioning said tube pinchers to periodically open and close said I.V. tubes at appropriate times to enable said syringe means to sequentially perform said fill and pump strokes said valve control means including a dual surface cam and a single cam follower for controlling substantially simultaneous snap action positioning of both of said tube pinchers so that said positioning maintains a one tube always open and one tube always closed relationship.

14. Apparatus as set forth in claim 13, and further comprising:
a pincher position sensor for generating an output electrical signal indicating the proper direction of rotation of said motor means in driving said syringe means.

15. Apparatus as set forht in forth 13, wherein both of said tube pinchers are biased towards the tube clamping off position and said valve control means includes a slide bar adapted to reciprocate along a linear path between said tube pinchers to alternately move one of said tube pinchers and then the other of said tube pinchers to the tube open position.

16. Apparatus as set forth in claim 15, wherein said slide bar reciprocates between two positions, and each end of said slide bar alternately contacts or is spaced away from the adjacent one of said tube pinchers depending upon which of said two positions is assumed by said slide bar.

17. In a system for parenteral administration of liquids from a liquid source to a patient, apparatus comprising:
a housing;
syringe means supported by said housing for performing alternate fill and pump strokes to control the flow of liquid to a patient, said syringe means including intake and output I.V. tubes;
a pair of movable tube pinchers adjacent said I.V. tubes, one for each of said I.V. tubes, for alternately clamping off and opening the associated I.V. tube, said tube pinchers being spring biased towards the tube clamping off point;
motor means within said housing for driving said syringe means for performance of said fill and pump strokes;
valve control means within said housing for alternately positioning said tube pinchers to periodically open and close said I.V. tubes at appropriate times to enable said syringe means to sequentially perform said fill and pump strokes. said valve control means including a slide bar adapted to move along a linear path between said tube pinchers to alternately move one of said tube pinchers and then the other of said tube pinchers to the tube open position, and slide bar reciprocating between two positions, each end of said slide bar alternately contacting or being spaced away from the adjacent one of said tube pinchers depending upon which of said two positions is assumed by said slide bar;
a rotary cam driven by said motor means, said cam having an arcuate, semi-circular ridge defining inner and outer cam surfaces;
a slide bar pin projecting from one face of said slide bar and engaging one or the other of said inner and outer cam surfaces; and
a slide bar spring, one end of said slide bar spring being secured to the center of said slide bar, the other end of said slide bar spring being secured to said rotary cam.

18. Apparatus as set forth in claim 17, wherein the center of said slide bar is offset from the center of rotation of said cam in either of said two positions of said slide bar.

19. Apparatus as set forth in claim 17, and further including:
a reference light source and photoelectric sensor maintained in a fixed position; and
an opaque member carried by one of said tube pinchers and adapted to interrupt the light beam from said reference light source in one position of the tube pincher while being withdrawn from said light beam in the other position of said tube pincher, whereby an electrical signal is generated indicating the required direction of rotation of said motor.

20. Apparatus as set forth in claim 17, wherein said ridge defines a 180° arc.

21. Apparatus as set forth in claim 17, wherein said other end of said slide bar spring is secured to said rotary cam adjacent the outer periphery of said cam.

22. In a syringe pump having a housing and including a syringe supported within the housing, apparatus comprising:
driving means for driving the syringe through a fill stroke in which the syringe is filled with fluid through an intake line and through a pump stroke during which fluid is delivered from the syringe through an output line;
movable tube pincher means for alternately opening and closing said intake and output lines in proper sequence for performance of said fill and pump strokes; and
sensing means responsive to said tube pincher means for determining the direction of movement of said driving means.

23. Apparatus as set forth in claim 22, wherein said driving means is an electrical motor and said sensing means generates an electrical signal for establishing the direction of rotation of said motor.

24. In a syringe pump, apparatus comprising:

an intake pivotal tube pincher for alternately clamping off and opening an intake I.V. tube;

an output pivotal tube pincher for alternately clamping off and opening an output I.V. tube;

a pincher spring secured at one end to said intake tube pincher and at the other end to said output tube pincher, said pincher spring extending between said tube pinchers and biasing said tube pinchers towards the tube clamping off position;

a slide bar adapted to reciprocate along a linear path between said tube pinchers to alternately and sequentially move one of said tube pinchers and then the other of said tube pinchers to the tube open position;

a reversible, rotary cam having an arcuate, semi-circular ridge defining inner and outer camming surfaces, said ridge defining a 180° arc; a slide bar pin projecting from one face of said slide bar and engaging one or the other of said inner and outer camming surfaces;

a slide bar spring, one end of said slide bar spring being secured to the center of said slide bar, the other end of said slide bar spring being secured to the outer periphery of said rotary cam;

reversible, electrical motor means for rotating said rotary cam in either of two directions;

a reference light source and photoelectric sensor maintained in a fixed position; and an opaque member carried by one of said tube pinchers and adapted to interrupt the reference light beam from said light source in one position of the tube pincher while being withdrawn from said reference light beam in the other position of the tube pincher, whereby an electrical signal is generated indicating the required direction of rotation of said motor.

25. Apparatus as set forth in claim 24, wherein said slide bar reciprocates between two positions, and each end of said slide bar alternately contacts or is spaced away from the adjacent one of said tube pinchers depending upon which of said two positions is assumed by said slide bar.

26. Apparatus as set forth in claim 25, wherein the center of said slide bar is offset from the center of rotation of said cam in either of said two positions of said slide bar.

27. Apparatus as set forth in claim 26, wherein each of said tube pinchers is substantially L-shpaed having a longer arm and a shorter arm.

28. Apparatus as set forth in claim 27, wherein one edge of said shorter arm defines a tube pincher blade adapted to clamp off an I.V. tube.

29. Apparatus as set forth in claim 26, wherein each end of said slide bar is fitted with a bumper pad through which said slide bar alternately contacts said tube pinchers.

30. In a syringe pump, the combination comprising;
a housing;
a syringe supported within said housing and having inlet and outlet ports and a piston slidably received within said syringe, said syringe having no valves for said inlet and outlet ports;
drive means within said housing for reciprocating said syringe piston;
an intake I.V. tube coupled to said inlet port;
an outlet I.V. tube coupled to said outlet port; valve means associated with said tubes; and valve control means within said housing separate from said syringe for cyclically opening and closing said valve means and thereby said intake and output I.v. tubes at appropriate times to enable said syringe to sequentially perform fill and pump strokes. said control means including a dual surface cam and a single cam follower for effecting substantially simultaneous snap action control over the opening and closing of said intake and output I.V. tubes which maintains a one tube always open and one tube always closed relationship.

31. In a syringe pump, apparatus comprising:
an intake I.V. tube and output I.V. tube;
an intake tube pincher for alternately clamping off and opening said intake I.V. tube;
an output tube pincher for alternately clamping off and opening said output I.V. tube; said pinchers being movably mounted with respect to one another;
a pincher spring secured at one end to said intake tube pincher and at the other end to said output tube pincher, said pincher spring extending between said tube pinchers and biasing said tube pinchers towards the tube clamping off position;
a tube pincher control means for alternately and sequentially moving one of said tube pinchers and then the other of said tube pinchers to the tube open position;
a reversible, rotary cam having an arcuate, semi-circular ridge defining inner and outer camming surfaces;
a single cam follower coupled to said pincher control means and engaging one or the other of said inner and outer camming surfaces; and
reversible, electrical motor means for rotating said rotary cam in either of two direction.

32. In a syringe pump, apparatus comprising:
a housing;
an intake I.F. tube and output I.V. tube;
an intake tube pincher within said housing for alternately clamping off and opening said intake I.V. tube;
an output tube pincher within said housing for alternately clamping off and opening said output I.V. tube; said tube pinchers being movably mounted with respect to one another;
a pincher spring secured at one end to said intake tube pincher and at the other end to said output tube pincher, said pincher spring extending between said tube pinchers and biasing said tube pinchers towards the tube clamping off position;
a tube pincher control means within said housing for alternately and sequentially moving one of said tube pinchers and then the other of said tube pinchers to the tube open position, said tube pincher control means including a single common member for substantially simultaneous snap action positioning both of said tube pinchers so that said positioning maintains a one tube always open and one tube alwasy closed relationship.

33. Apparatus as set forth in claim 32, and further comprising:
a reversible rotary cam;
a single cam follower coupled to said pincher control means and engaging said cam; and
reversible, electrical motor means for rotating said rotary cam in either of two directions.

34. In a syringe pump having a housing and intake and output I.V. tubes, the combination comprising:
a pair of movable tube pinchers within the housing;
drive means within the housing for positioning said tube pinchers to open and close said I.V. tubes;
reversible cam means;
cam follower means;
spring means for biasing said cam follower means against surfaces of said cam means in both directions of said cam control means; and
a single common member, coupled to said cam follower means for controlling substantially simultaneous snap action positioning and repositioning of said tube pinchers so that said positioning maintains a one tube always open and one tube always closed relationship.

* * * * *

UNITED STATES PATENT OFFICE
CERTIFICATE OF CORRECTION

Patent No. 3,994,294          Dated November 30, 1976

Inventor(s) Knute, Wallace L.

It is certified that error appears in the above-identified patent and that said Letters Patent are hereby corrected as shown below:

Column 1, line 20, delete "trypically" and insert therefor --typically--.

Column 6, line 17, delete "1965" and insert therefor --1975--; lines 18-20, delete the sentence beginning "A copy of" and ending "Appendix A.".

Column 7, lines 34-35, delete "becu-ase" and insert therefor --because--; line 68, delete "tupe" and insert therefor --tube--.

Column 9, line 39, delete "simultaneouus" and insert therefor --simultaneous--.

Column 10, line 20, delete "1" and insert therefor --7--; line 43, after "of" insert --spring biased--.

Column 11, line 8, delete "fo" and insert therefor --of--; line 43, delete "forht in"; after "forth" insert --in Claim--.

UNITED STATES PATENT OFFICE
CERTIFICATE OF CORRECTION

Patent No. 3,994,294           Dated November 30, 1976

Inventor(s)   Knute, Wallace L.

It is certified that error appears in the above-identified patent and that said Letters Patent are hereby corrected as shown below:

Column 13, line 49, delete "shpaed" and insert therefor --shaped--.

Column 14, line 4, delete "I.v." and insert therefor --I.V.--; line 40, delete "I.F." and insert therefor --I.V.--; line 61, delete "alwasy" and insert therefor --always--.

Signed and Sealed this

*Fifteenth* Day of *November 1977*

[SEAL]

*Attest:*

RUTH C. MASON
*Attesting Officer*

LUTRELLE F. PARKER
*Acting Commissioner of Patents and Trademarks*